(12) United States Patent
Oh et al.

(10) Patent No.: US 12,329,846 B2
(45) Date of Patent: Jun. 17, 2025

(54) METHOD FOR PREPARING MICROCAPSULE

(71) Applicants: LG HOUSEHOLD & HEALTH CARE LTD., Seoul (KR); LG CHEM, LTD., Seoul (KR)

(72) Inventors: Jung Whan Oh, Daejeon (KR); Kyung On Cha, Daejeon (KR); Ji Won Kim, Daejeon (KR); Jee Seon Kim, Daejeon (KR); Chanjoong Kim, Daejeon (KR); Sangryeo Lee, Daejeon (KR); Minchae Kim, Daejeon (KR); Myeongho Kim, Daejeon (KR)

(73) Assignees: LG HOUSEHOLD & HEALTH CARE LTD., Seoul (KR); LG CHEM, LTD., Seoul (KR)

( * ) Notice: Subject to any disclaimer, the term of this patent is extended or adjusted under 35 U.S.C. 154(b) by 914 days.

(21) Appl. No.: 17/268,769

(22) PCT Filed: Aug. 23, 2019

(86) PCT No.: PCT/KR2019/010790
§ 371 (c)(1),
(2) Date: Feb. 16, 2021

(87) PCT Pub. No.: WO2020/040608
PCT Pub. Date: Feb. 27, 2020

(65) Prior Publication Data
US 2021/0338561 A1  Nov. 4, 2021

(30) Foreign Application Priority Data

Aug. 24, 2018  (KR) .................. 10-2018-0099491
Aug. 22, 2019  (KR) .................. 10-2019-0103288

(51) Int. Cl.

| | | |
|---|---|---|
| *A61K 8/86* | (2006.01) | |
| *A61K 8/06* | (2006.01) | |
| *A61K 8/11* | (2006.01) | |
| *A61Q 1/02* | (2006.01) | |
| *A61Q 13/00* | (2006.01) | |
| *B01J 13/16* | (2006.01) | |
| *C11D 3/12* | (2006.01) | |
| *C11D 3/37* | (2006.01) | |
| *C11D 3/40* | (2006.01) | |
| *C11D 3/50* | (2006.01) | |
| *C11D 11/00* | (2006.01) | |
| *C11D 17/00* | (2006.01) | |

(52) U.S. Cl.
CPC .............. *A61K 8/86* (2013.01); *A61K 8/062* (2013.01); *A61K 8/11* (2013.01); *A61Q 1/02* (2013.01); *A61Q 13/00* (2013.01); *B01J 13/16* (2013.01); *C11D 3/1213* (2013.01); *C11D 3/124* (2013.01); *C11D 3/3703* (2013.01); *C11D 3/40* (2013.01); *C11D 3/505* (2013.01); *C11D 11/0082* (2013.01); *C11D 17/0039* (2013.01); *A61K 2800/412* (2013.01); *A61K 2800/43* (2013.01); *A61K 2800/56* (2013.01); *A61K 2800/805* (2013.01); *C11D 2111/12* (2024.01)

(58) Field of Classification Search
None
See application file for complete search history.

(56) References Cited

U.S. PATENT DOCUMENTS

| | | |
|---|---|---|
| 5,804,298 A | 9/1998 | Moy |
| 2005/0204958 A1 | 9/2005 | Kuebelbeck et al. |
| 2008/0220176 A1 | 9/2008 | Carlblom et al. |
| 2009/0181254 A1 | 7/2009 | White et al. |
| 2016/0168508 A1 | 6/2016 | Ribaut et al. |
| 2016/0317993 A1 | 11/2016 | Rotello et al. |
| 2017/0049667 A1 | 2/2017 | Shimizu et al. |
| 2018/0272308 A1 | 9/2018 | Sasaki et al. |
| 2019/0255502 A1 | 8/2019 | Wu et al. |

FOREIGN PATENT DOCUMENTS

| | | |
|---|---|---|
| CN | 103506059 A | 1/2014 |
| CN | 105431227 A | 3/2016 |
| JP | 5-212272 A | 8/1993 |
| KR | 10-2004-0094760 A | 11/2004 |
| KR | 10-2013-0142268 A | 12/2013 |
| KR | 10-2016-0145824 A | 12/2016 |
| WO | WO 2017/058875 A1 | 4/2017 |
| WO | WO 2018/054719 A1 | 3/2018 |

OTHER PUBLICATIONS

Williams et al., Journal of Colloid and Interface Science 460 (2015) 71-80 (Year: 2015).*
Stealey et al., Pharmaceuticals 2023, 16, 821 (Year: 2023).*
Zhang et al, Ind. Eng. Chem. Res. 2014, 53, 12330-12338 (Year: 2014).*

(Continued)

*Primary Examiner* — David J Blanchard
*Assistant Examiner* — Edwin Coleman Mitchell
(74) *Attorney, Agent, or Firm* — Birch, Stewart, Kolasch & Birch, LLP

(57) ABSTRACT

The present disclosure provides a method for preparing a microcapsule and a microcapsule prepared thereby capable of selective release of oils and preventing volatilization of oils while maintaining long-term performance by improving storage stability of the oil contained in the capsule.

10 Claims, 8 Drawing Sheets

(56) References Cited

OTHER PUBLICATIONS

AquaCalc, Density of Sunflower Oil, UPC, https://www.aqua-calc.com/page/density-table/substance/sunflower-blank-oil-coma-and-blank-upc-column--blank-857408002019 (Year: 2023).*

Wu et al., Hybrid microcapsules with tunable properties via Pickering emulsion templates for the encapsulation of bioactive volatiles RSC Adv., 6, 102595, published 2016 (Year: 2016).*

Lee et al., Microencapsulation of fragrant oil via in situ polymerization: effects of pH and melamine-formaldehyde molar ratio, j. microencapsulation, vol. 19, No. 5, 559±569, published 2002 (Year: 2002).*

Zhang et al., "Improving Stability and Sizing Performance of Alkenylsuccinic Anhydride (ASA) Emulsion by Using Melamine-Modified Laponite Particles as Emulsion Stabilizer", Industrial & Engineering Chemistry Research, vol. 53, 2014, pp. 12330-12338.

International Search Report for PCT/KR2019/010790 mailed on Dec. 9, 2019.

Williams et al., "Inorganic/organic hybrid microcapsules: Melamine formaldehyde-coated Laponite-based Pickering emulsions", Journal of Colloid and Interface Science, 2015, vol. 460, pp. 71-80.

Wu et al., "Hybrid Microcapsules with Tunable Properties via Pickering Emulsion Templates for the Encapsulation of Bioactive Volatiles", RSC Advances, 2016, pp. 1-24.

Yin et al., Fabrication and performance of microencapsulated phase change materials with hybrid shell by in situ polymerization in Pickering emulsion, Polymers for Advanced Technologies, 2015, vol. 26, pp. 613-619.

* cited by examiner

【FIG. 1】
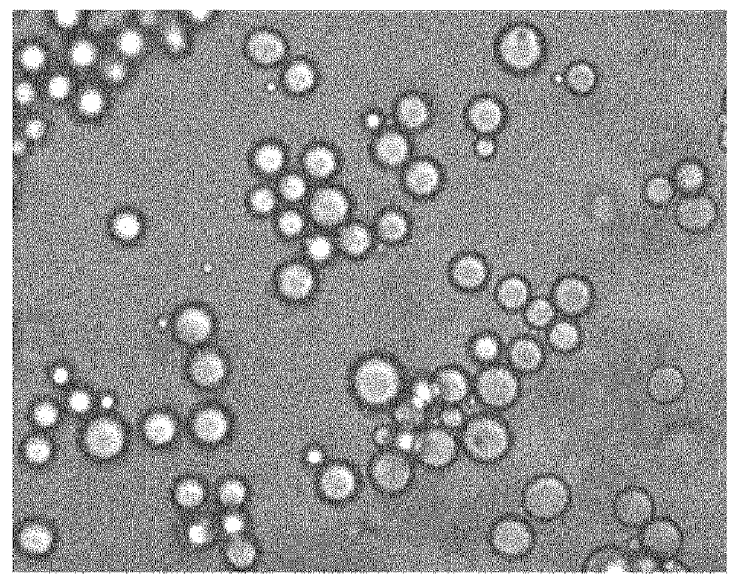
【FIG. 2】
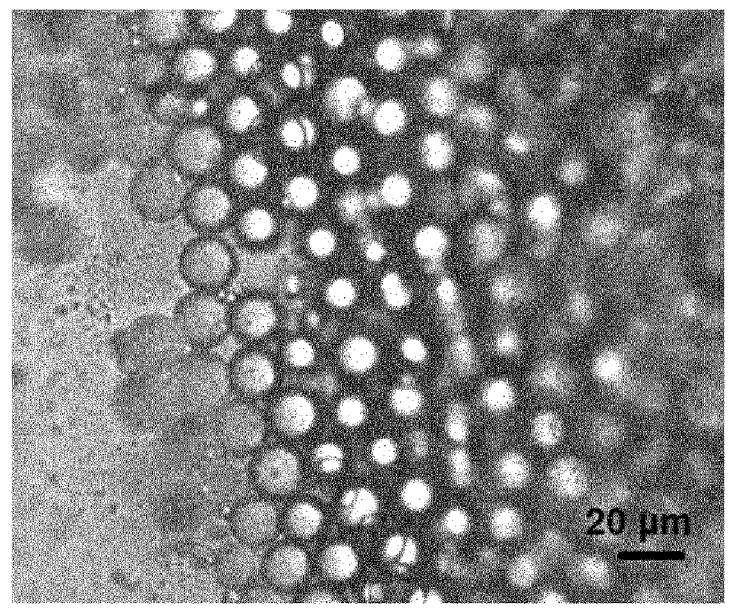

【FIG. 3】
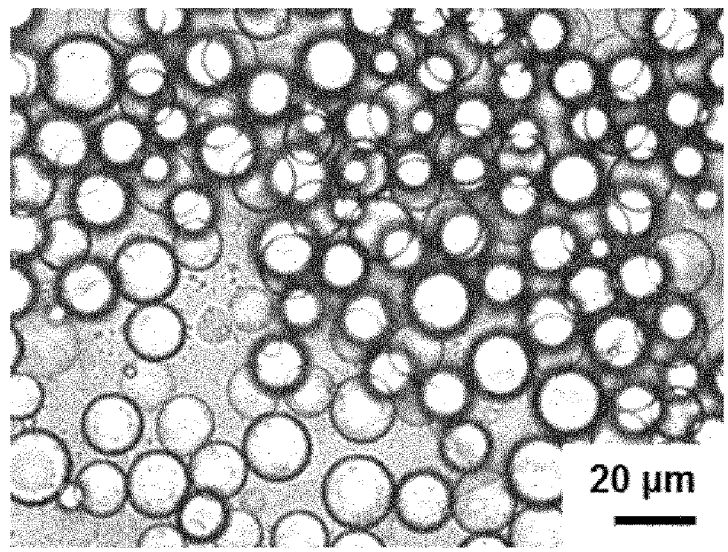
【FIG. 4】
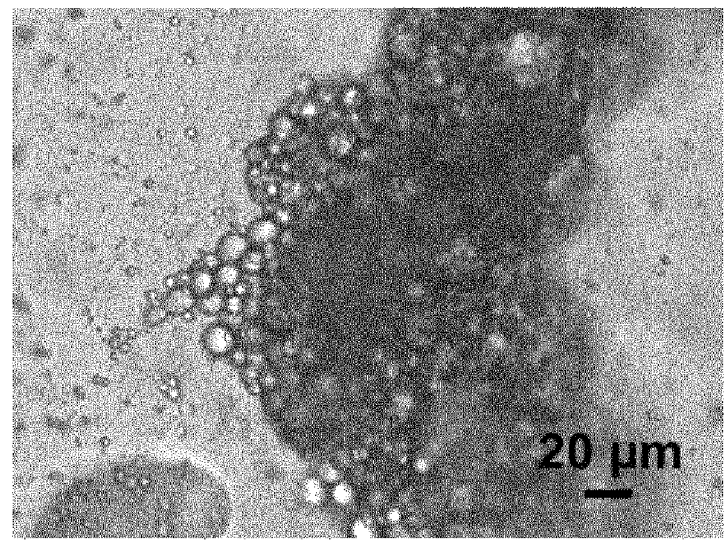

【FIG. 5】
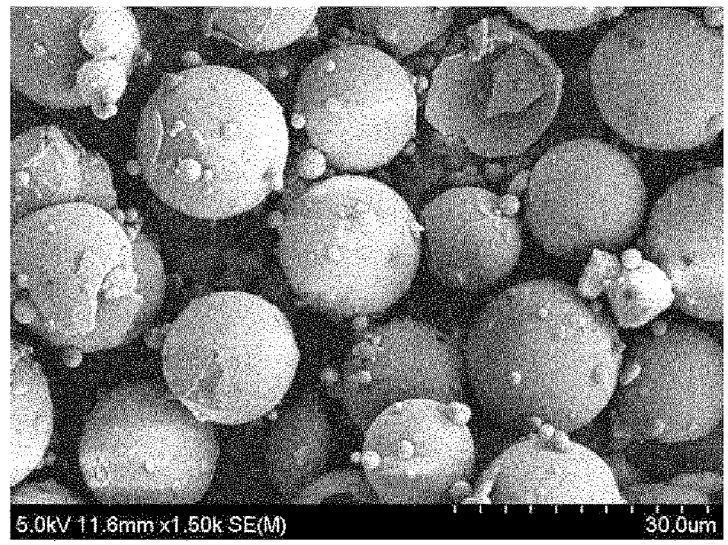
【FIG. 6】
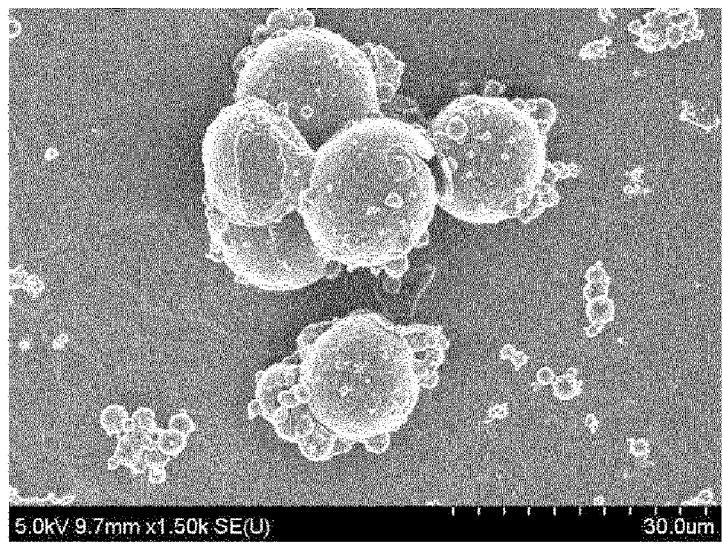

【FIG. 7】
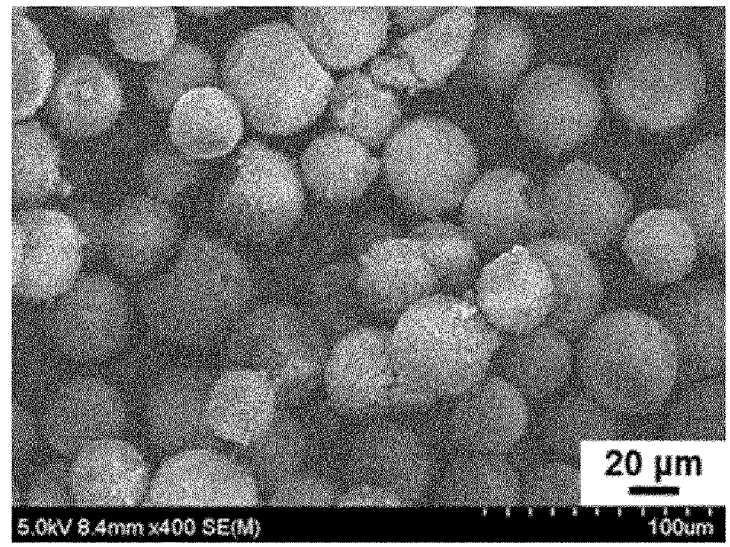
【FIG. 8】
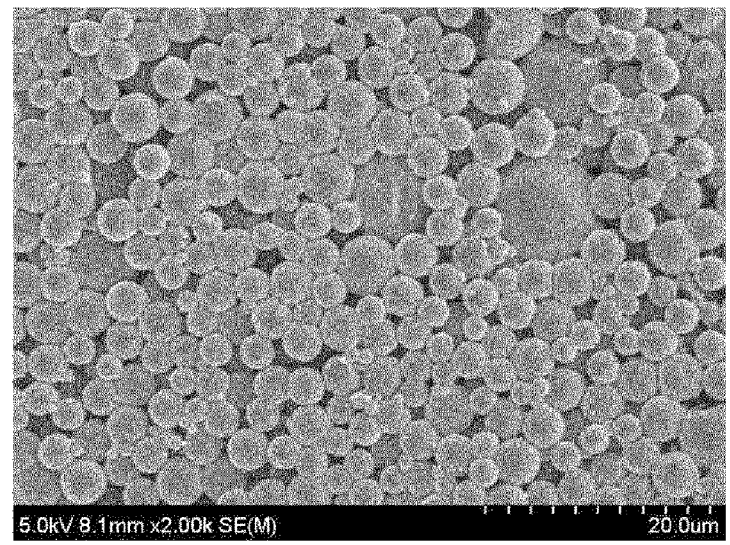

【FIG. 9】
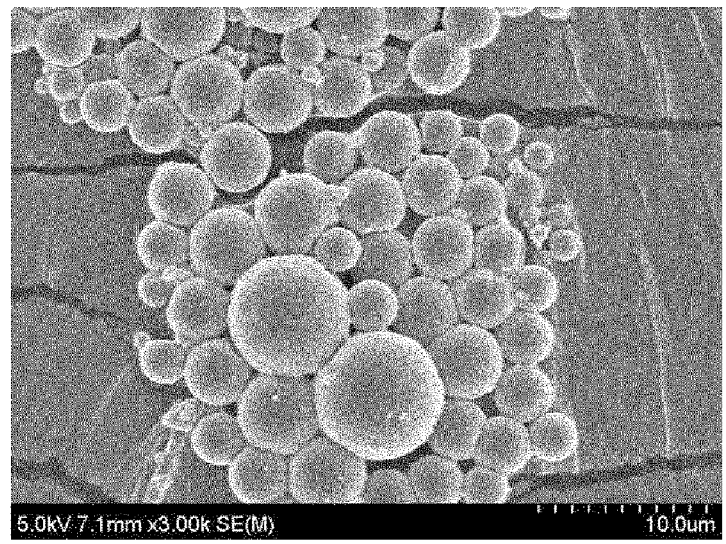
【FIG. 10】
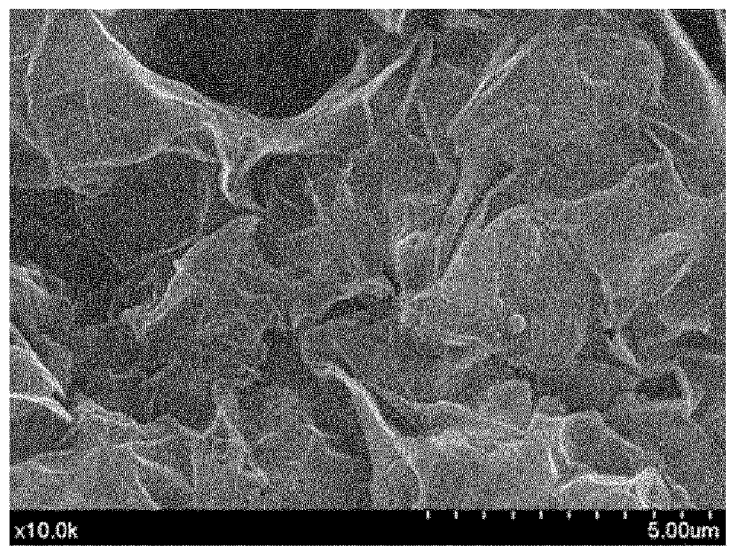

[FIG. 11]
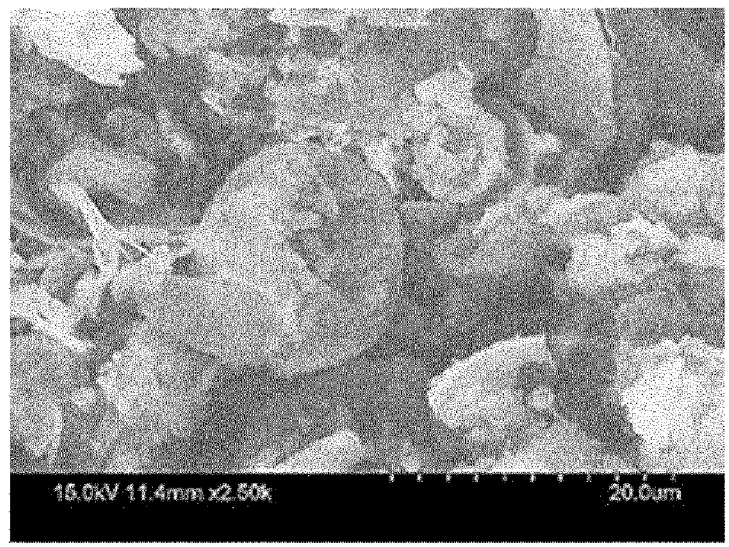
[FIG. 12]
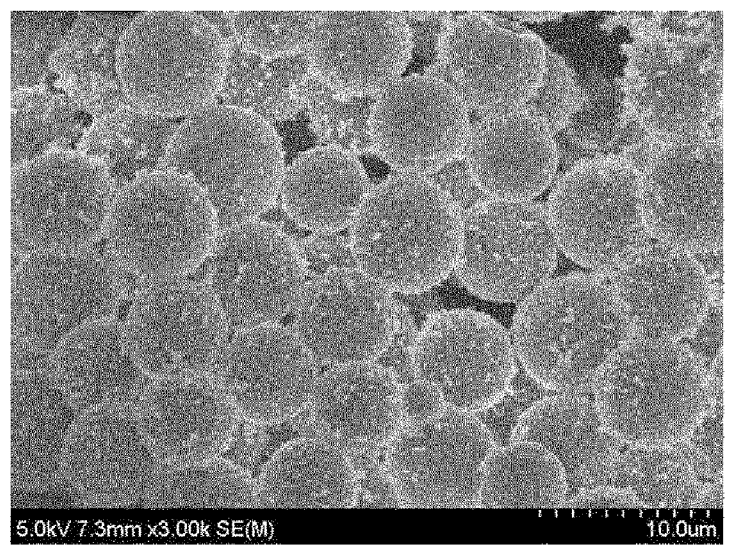

[FIG. 13]
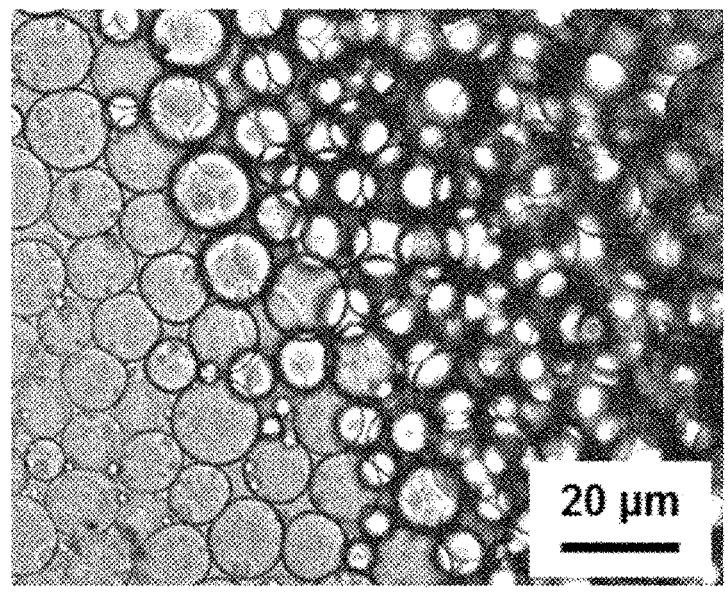
[FIG. 14]
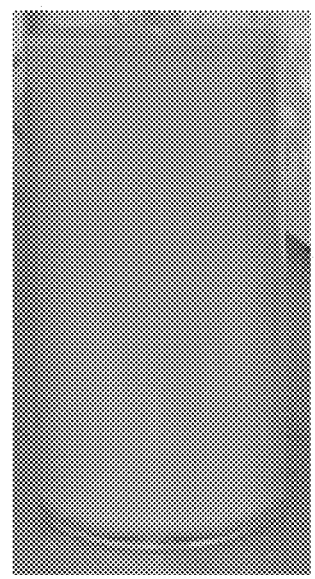

[FIG. 15]
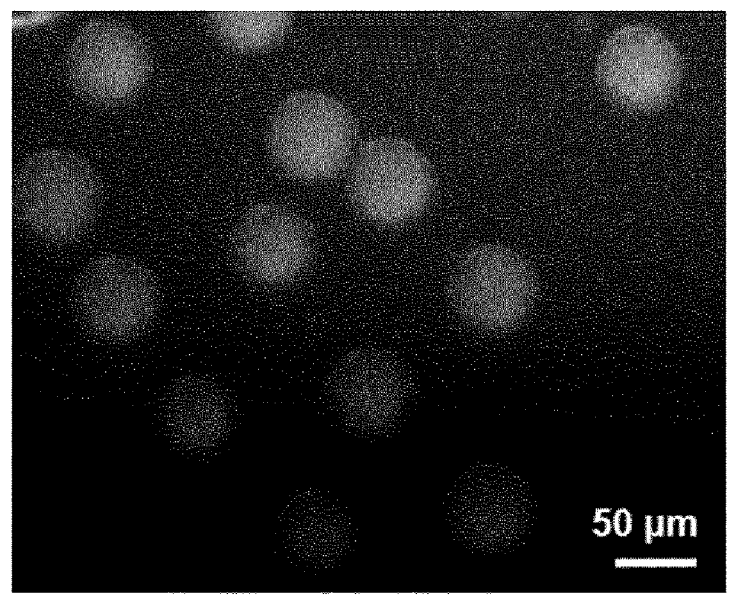

METHOD FOR PREPARING MICROCAPSULE

CROSS-REFERENCE TO RELATED APPLICATION(S)

This application claims the benefits of Korean Patent Applications No. 10-2018-0099491 filed on Aug. 24, 2018 and No. 10-2019-0103288 filed on Aug. 22, 2019 with the Korean Intellectual Property Office, the disclosure of which is incorporated herein by reference in its entirety.

TECHNICAL FIELD

The present disclosure relates to a method for producing a microcapsule.

BACKGROUND ART

Microcapsules are widely used for a variety of purposes. For example, they can be used for various purposes such as colorants, catalysts, adhesives, fragrances, fuels, pesticides, biomaterials, clothing, insect repellents, pharmaceuticals, food, cosmetics, household goods, and detergents. In particular, oil-containing microcapsules used for household goods such as clothing, insect repellents, pharmaceuticals, cosmetics and detergents should not release the oil from the capsule during distribution, and the oil contained in the capsule should be released when using the product. For example, fragrance oils should release a certain amount of fragrance that can be sensed by a user at the time of using the product.

However, most of the conventional methods for preparing a microcapsule form the oil into emulsion droplets using a monomolecular or polymer type surfactant, and then perform a polycondensation reaction of a resin such as melamine-formaldehyde, urea or urethane on a surface of the emulsion oil droplets to encapsulate. Oil capsules thus prepared are excellent in initial oil loading capacity and efficiency, but are difficult to block the release of oil during storage and distribution. For example, the melamine-formaldehyde resin is mainly used for the preparation of a microcapsule because of excellent mechanical and thermal stability and simple manufacturing process. The method for preparing a microcapsule using the melamine-formaldehyde resin is as follows: the oil is emulsified using at least one anionic polymer emulsifier, and then polymerization/adsorption of a melamine-formaldehyde pre-polymer is induced on a surface of the emulsion prepared at an acidic pH to prepare a microcapsule. In this method, it is difficult to manufacture a large capsule, and a content of oil contained in the capsule is low. In addition, there is a problem in that material permeability of the capsule film is high due to the anionic polymer used as an emulsifier, so that the oil cannot be stably loaded.

Thus, a method for preparing a stabilized microcapsule using inorganic nanoparticles has been proposed. This method is to prepare a pickering emulsion by controlling surface wettability of inorganic materials such as silica and using the inorganic materials as an emulsifier. The pickering emulsion composed of inorganic materials may form an inorganic membrane through which collected molecules cannot permeate, but there is a problem in that random leakage of the collected molecules cannot be prevented due to porosity of the capsule.

DETAILED DESCRIPTION OF THE PRESENT DISCLOSURE

Technical Problem

The present disclosure is to provide a method for preparing a microcapsule capable of selective release of oils and preventing volatilization of oils while maintaining long-term performance by improving storage stability of the oil contained in the capsule, especially a fragrance oil or an oil for color formation.

Technical Solution

According to an embodiment of the present disclosure, there is provided a method for preparing a microcapsule, including a first step of mixing an aqueous dispersion of hydrophilic inorganic nanoparticles with an aqueous solution of a melamine-based monomolecular compound to prepare an aqueous dispersion of organic/inorganic composite particles in which melamine is bonded to a surface of the hydrophilic inorganic nanoparticles by electrostatic attraction;

a second step of adding an oil to the aqueous dispersion of organic/inorganic composite particles to form an oil-in-water pickering emulsion (O/W pickering emulsion); and a third step of adding a melamine-formaldehyde precondensate to the oil-in-water pickering emulsion, and performing a polycondensation reaction.

According to another embodiment of the present disclosure, there is provided a microcapsule prepared by the above method having a core-shell structure including a core containing an oil surrounded by hydrophilic inorganic nanoparticles in which melamine is surface-bonded by electrostatic attraction; and a shell surrounding the core and containing a melamine-formaldehyde resin.

Advantageous Effects

A microcapsule capable of selective release of oils and preventing volatilization of oils while maintaining long-term performance can be prepared according to the above method of the present disclosure by improving storage stability of the oil contained in the capsule. Particularly, when the oil contained in the microcapsule is a volatile fragrance oil, volatilization of the fragrance oil can be prevented and the fragrance oil can be selectively released. When the oil is an oil for color formation, the reaction of the oil for color formation can be inhibited even in the state of aqueous dispersion, thereby maintaining its performance for a long time.

BRIEF DESCRIPTION OF DRAWINGS

FIG. 1 is an optical microscope observation image of the microcapsule prepared in Example 1 (magnification: ×200).

FIG. 2 is an optical microscope observation image of the oil-in-water pickering emulsion in Example 1.

FIG. 3 is an optical microscope observation image of the oil-in-water pickering emulsion in Example 3.

FIG. 4 is an optical microscope observation image of the oil-in-water pickering emulsion in Comparative Example 3.

FIGS. 5 to 12 are electron microscope images of the microcapsules prepared in Examples 1 to 3, Comparative Examples 1 to 4 and Reference Example 1, respectively.

FIG. 13 is an optical microscope observation image of the oil-in-water pickering emulsion prepared in Example 4.

FIG. 14 is a photograph of the aqueous dispersion of the microcapsule prepared in Example 4.

FIG. 15 is a fluorescence microscope image of the microcapsule prepared in Example 4.

DETAILED DESCRIPTION OF THE EMBODIMENTS

Hereinafter, the present disclosure will be described in more detail. As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

The terms "include", "comprise", and the like of the present disclosure are used to specify certain features, regions, integers, steps, operations, elements, and/or components, and these do not exclude the existence or the addition of other certain features, regions, integers, steps, operations, elements, and/or components.

Hereinafter, the method for preparing a microcapsule and the microcapsule prepared thereby will be described.

The method for preparing a microcapsule according to an embodiment of the present disclosure includes a first step of mixing an aqueous dispersion of hydrophilic inorganic nanoparticles with an aqueous solution of a melamine-based monomolecular compound to prepare an aqueous dispersion of organic/inorganic composite particles in which melamine is bonded to a surface of the hydrophilic inorganic nanoparticles by electrostatic attraction;

a second step of adding an oil to the aqueous dispersion of organic/inorganic composite particles to form an oil-in-water pickering emulsion (O/W pickering emulsion); and a third step of adding a melamine-formaldehyde precondensate to the oil-in-water pickering emulsion, and performing a polycondensation reaction.

As described above, the method for preparing a microcapsule according to an embodiment of the present disclosure improves surface wettability of hydrophilic inorganic nanoparticles by using a melamine-based monomolecular compound having a polyfunctional amine group. In addition, the method forms a stable oil-in-water emulsion using a pickering emulsion method, followed by a polycondensation reaction of a melamine-formaldehyde precondensate to form a shell layer of the melamine-formaldehyde resin, thereby preparing a microcapsule having a core-shell structure.

Specifically, a first step of the method for preparing a microcapsule according to an embodiment of the present disclosure prepares hydrophilic inorganic nanoparticles with improved surface wettability by mixing an aqueous dispersion of hydrophilic inorganic nanoparticles with controlled pH and a melamine-based monomolecular compound, and adsorbing melamine molecules on a surface of the hydrophilic inorganic nanoparticles specifically by electrostatic attraction.

The aqueous dispersion of hydrophilic inorganic nanoparticles may be prepared by dispersing the hydrophilic inorganic nanoparticles in water.

At this time, a pH of the aqueous dispersion of hydrophilic inorganic nanoparticles prepared may be 4 to 9, more specifically 4 to 7. Within the above pH range, the surface of the hydrophilic inorganic nanoparticles may be negatively charged and uniformly dispersed in the dispersion medium, and as a result, melamine may be efficiently bonded by electrostatic attraction. When the pH of the aqueous dispersion of hydrophilic inorganic nanoparticles exceeds 9 out of the above range, solubility and cationicity of the melamine molecules may be lowered, thereby reducing a modification efficiency of the particle surface. When the pH is less than 4, solubility of the melamine molecules is greatly increased, so that the modified nanoparticles may not stably form an emulsion. Accordingly, if necessary, the pH of the aqueous dispersion of hydrophilic inorganic nanoparticles may be adjusted to the above range, preferably 4 to 9, by adding an acidic aqueous solution such as sulfuric acid, nitric acid, or hydrochloric acid, or an alkaline aqueous solution such as sodium hydroxide or sodium carbonate.

Meanwhile, the hydrophilic inorganic nanoparticles are spherical hydrophilic inorganic particles having a nano-level particle size (or particle diameter) of 1 nm or more and less than 1 μm. Specifically, a volume-based average particle diameter ($D_{50}$) may be 1 to 300 nm. When the average particle diameter ($D_{50}$) of the hydrophilic inorganic nanoparticles is too small, dispersibility may be reduced due to excessive aggregation of the particles, and when too large, dispersibility may be reduced due to the particles themselves. Accordingly, excellent dispersibility may be stably exhibited when having a particle size within the above range. More specifically, the hydrophilic inorganic nanoparticles preferably have an average particle diameter ($D_{50}$) of 5 to 200 nm at a pH 4 to 9 to appropriately control the capsule size and stably load the oil by excellent dispersibility and dispersion stability.

The average particle diameter ($D_{50}$) can be calculated from a volume cumulative value measured with a laser diffraction scattering particle size analyzer.

Specific examples of the hydrophilic inorganic nanoparticles include silica, titania, metal oxides, noble metals, apatite, limestone and the like, and any one or a mixture of two or more of the above materials may be used according to the use of the microcapsule and the type of oil. In particular, the hydrophilic inorganic nanoparticles may be silica having the same surface charge throughout the particle. Some inorganic particles may be charged with either negative or positive charges depending on the particle surface. When inducing bonding by electrostatic attraction of one monomolecular compound, only a specific part is modified and the rest may have repulsion by maintaining an electrostatic property as it is, resulting in a decrease in the film density of the capsule to be prepared. In contrast, the silica has the same surface charge, which allows homogeneous bonding of melamine by electrostatic attraction, resulting in an increase in the film density.

In addition, a content of the hydrophilic inorganic nanoparticles in the aqueous dispersion of hydrophilic inorganic nanoparticles is not particularly limited. However, it is preferable to include the hydrophilic inorganic nanoparticles in an amount of 0.01 to 1.0 wt % based on a total weight of the aqueous dispersion in consideration of processability, and the like.

The hydrophilic inorganic nanoparticles may be used in an amount of 0.1 wt % or more and 2 wt % or less based on a total weight of the microcapsule to be prepared. When the hydrophilic inorganic nanoparticles are used in less than 0.1 wt %, the emulsion may not be formed. When the hydrophilic inorganic nanoparticles are used in greater than 2 wt %, a diameter of the emulsion may be very small and dispersion stability may be lowered. The hydrophilic inorganic nanoparticles may preferably be used in 0.3 wt % or more, 0.4 wt % or more, or 0.5 wt % or more, and 2.0 wt % or less, 1.8 wt % or less, or 1.5 wt % or less based on a total weight of the microcapsule to be prepared to further improve the properties.

The aqueous solution of the melamine-based monomolecular compound is prepared by dissolving melamine or a derivative thereof in water. If necessary, the pH of the aqueous solution of the melamine-based monomolecular compound may be adjusted to 4 to 7 by adding an acidic aqueous solution such as hydrochloric acid, sulfuric acid, or acetic acid. In the aqueous solution with the above pH, the melamine is present as a positively charged molecule.

The melamine-based monomolecular compound used in the present disclosure is a monomolecular compound of melamine or a derivative thereof, and specifically, may have a weight average molecular weight of 70 to 200 g/mol, more specifically 100 to 150 g/mol.

As described above, when preparing organic/inorganic composite particles for a pickering emulsion, a monomolecular compound of melamine or a derivative thereof having a lower molecular weight than a polymer is used. Thus, the melamine can be uniformly bonded to a surface of the hydrophilic inorganic nanoparticles by electrostatic attraction, and as a result, surface wettability of the hydrophilic inorganic nanoparticles can be homogeneously modified. In addition, when a polymer is used, aggregation between particles is likely to occur, and thus dispersion stability of the emulsion before encapsulation may be lowered.

A content of the melamine-based monomolecular compound in the aqueous solution of the melamine-based monomolecular compound is not particularly limited. However, it is preferable to include the melamine-based monomolecular compound in an amount of 0.1 to 40 wt % based on a total weight of the aqueous solution of the melamine-based monomolecular compound in consideration of solubility of melamine.

Mixing of the aqueous dispersion of hydrophilic inorganic nanoparticles with the aqueous solution of a melamine-based monomolecular compound may be performed according to a conventional mixing method. At this time, a treatment such as mechanical stirring may be further performed in order to increase the mixing efficiency and the bonding efficiency by electrostatic attraction.

The mixing of the aqueous dispersion of hydrophilic inorganic nanoparticles with the aqueous solution of a melamine-based monomolecular compound may be performed so that a content of the melamine-based monomolecular compound is 1 to 100 parts by weight based on 1 part by weight of the hydrophilic inorganic nanoparticles. When the content of the melamine-based monomolecular compound is too small, an amount of melamine molecules bonded to a surface of the hydrophilic inorganic nanoparticles by electrostatic attraction is small and it is difficult to obtain a sufficient effect. On the other hand, when the content of the melamine-based monomolecular compound is too high, the melamine-based monomolecular compound remaining unbonded on the surface of the hydrophilic inorganic nanoparticles may cause side reactions. When mixed in the above-described content range, melamine molecules may be bonded to the surface of the hydrophilic inorganic nanoparticles by electrostatic attraction without causing side reactions by the residual melamine-based monomolecular compound, thereby sufficiently realizing the effects of the present disclosure. The melamine-based monomolecular compound may preferably be mixed in 2 to 50 parts by weight based on 1 part by weight of the hydrophilic inorganic nanoparticles to further improve the properties.

The melamine may be included in an amount of 1 wt % or more and 4 wt % or less based on a total weight of the microcapsule to be prepared. Within the above range, the melamine is sufficiently bonded to the surface of the hydrophilic inorganic nanoparticles by electrostatic attraction, thereby improving surface wettability of the inorganic nanoparticles and realizing the effects of the present disclosure. The melamine may preferably be included in 1.5 wt % or more, or 2 wt % or more, and 3.5 wt % or less, 3.2 wt % or less, or 3 wt % or less based on a total weight of the microcapsule to be prepared to further improve the properties.

As a result of the mixing process, positively charged melamine molecules are bonded to the surface of the negatively charged hydrophilic inorganic nanoparticles by electrostatic attraction to form organic/inorganic composite particles, which are obtained in the form of nanostructures dispersed in water.

Subsequently, the second step is a step of forming an oil-in-water pickering emulsion (O/W pickering emulsion) by adding an oil to a silica nanocomposite dispersion in which melamine is surface-bonded by electrostatic attraction as a result of the first step.

The oil is used as an inner core material of the capsule, and may specifically include a fragrance oil or an oil for color formation.

Specific examples of the fragrance oil include an essential oil such as thyme, lemongrass, lavender, citronella, *eucalyptus* and geraniol, a mineral oil, a vegetable oil, and the like, but are not limited thereto. Any oil well known in the art may be used as long as it is a substance that can be emulsified in a liquid form.

In addition, the oil for color formation may be an oil having a color itself, or an oil containing a coloring agent, and the like. Specifically, the oil containing a coloring agent may include an oil dispersion coloring agent and a nonpolar hydrocarbon-based oil. Specifically, examples of the oil dispersion coloring agent include nile red, fluorescein, rhodamine, boron-dipyrromethene (BODIPY), a cyanine-based organic compound, an inorganic compound such as quantum dot, and the like. Any one or a mixture of two or more thereof may be used. In addition, examples of the nonpolar hydrocarbon-based oil include a C10 to C20 nonpolar hydrocarbon oil such as n-decane, n-dodecane, n-tetradecane, n-hexadecane, pentadecane, heptadecane, or octadecane. Any one or a mixture of two or more thereof may be used.

The oil may be included in an amount of 35 wt % or more and 90 wt % or less based on a total weight of the microcapsule to be prepared. When too little oil is included, the particle size is small and the effect of the oil is difficult to obtain. Further, the thickness of the capsule is relatively thick, so the release of active ingredients may not be easy. On the other hand, when too much oil is included, the performance of the capsule may be degraded due to poor stability of the emulsion. Thus, when the oil is included within the above range, the oil can be stably collected without the aforementioned concerns. The oil may preferably be included in 35 wt % or more, 50 wt % or more, or 70 wt % or more, and 88 wt % or less, or 85 wt % or less based on a total weight of the microcapsule to be prepared to further improve the properties.

When the oil is added to the emulsion of hydrophilic inorganic nanoparticles in which melamine is surface-bonded by electrostatic attraction in the first step, an oil-in-water pickering emulsion (O/W pickering emulsion) in which the oil is surrounded by the hydrophilic inorganic nanoparticles is produced. At this time, surface wettability of the hydrophilic inorganic nanoparticles is improved by the melamine bonded to the surface by electrostatic attraction through the treatment in the first step, so that the oil can be more stably collected.

The oil may be added in a conventional manner such as dropwise, and an ultrasonic dispersion or a homogenization dispersion treatment may be selectively performed to increase the mixing efficiency and the forming efficiency of the pickering emulsion after the addition of the oil.

Subsequently, the third step is a step of forming a shell layer of the outer melamine-formaldehyde resin by adding a melamine-formaldehyde precondensate to the oil-in-water pickering emulsion prepared in the second step, and performing a polycondensation reaction.

Specifically, the melamine-formaldehyde precondensate is added to the oil-in-water pickering emulsion prepared in the second step in an amount such that a content of a melamine-formaldehyde resin is 5 wt % or more and 60 wt % or less based on a total weight of the microcapsule to be prepared, followed by a polycondensation reaction.

The melamine-formaldehyde precondensate contains an imine functional group, and can rapidly synthesize a melamine-formaldehyde resin having a high molecular weight by rapidly reacting with a hydroxyl group or an amino group.

When too little melamine-formaldehyde precondensate is added, the formation of the shell layer containing the melamine-formaldehyde condensate may not be easy. When too much melamine-formaldehyde precondensate is added, an excessively thick shell layer may be formed, or particles or film layers may be synthesized alone to reduce dispersibility of the capsule. Thus, when the melamine-formaldehyde precondensate is added within the above range in consideration of the content of melamine-formaldehyde in the final microcapsule to be prepared, a melamine shell layer having an appropriate thickness is formed without a fear of side reactions, thereby exhibiting excellent oil collection and mechanical strength. The melamine-formaldehyde precondensate may preferably be included in 10 wt % or more, 12 wt % or more, or 14 wt % or more, and 60 wt % or less, 40 wt % or less, 30 wt % or less, or 25 wt % or less based on a total weight of the microcapsule to be prepared to adjust the thickness of the capsule and to further improve the mechanical strength.

Meanwhile, the melamine-formaldehyde precondensate may have a molar ratio of formaldehyde to melamine (molar ratio of formaldehyde/melamine) in the precondensate of 2 to 8. When the melamine-formaldehyde precondensate controlled in the above weight ratio range is used, excellent storage stability and excellent compatibility with water which is a dispersion medium may be exhibited without the addition of surfactants.

The polycondensation reaction may be carried out at a temperature of 50 to 90° C., and a heating process may be performed to make the temperature. When the temperature during the polycondensation reaction is within the above range, high reaction efficiency can be exhibited without a fear of unreacted or side reactions.

In addition, in order to increase the efficiency of the polymerization reaction during the polycondensation reaction, a stirring process may be performed at the same time. The stirring process may be performed at 300 to 1000 rpm, preferably at 500 to 600 rpm.

As the polymer resin prepared through the polycondensation reaction of the melamine-formaldehyde precondensate is continuously bonded to the emulsion surface, an outer shell layer (shell) is formed.

After the polymerization of the third step, a concentration or/and drying process may be further performed, if necessary, and the conditions are not limited.

The microcapsule prepared according to the method described above has a core-shell structure. The core contains an oil surrounded by hydrophilic inorganic nanoparticles in which melamine is surface-bonded by electrostatic attraction, and the shell has a multilayer structure of one or more layers and contains a melamine-formaldehyde resin. Accordingly, it is possible to provide a colloidal system more physically stabilized by an organic/inorganic composite emulsifier while still exhibiting properties of the surface melamine-formaldehyde resin capsule such as hardness and adhesion to fibers. In addition, the multilayered capsule can prevent unintentional release of oil molecules collected therein.

In addition, the microcapsule prepared by the above-described method may have an average particle diameter ($D_{50}$) of 5 μm or more and 50 μm or less, and an average thickness of the shell containing a melamine-formaldehyde resin may be 50 nm or more. Since the size of the capsule particles is large and the thickness of the shell is thick, a content of the oil contained in the capsule may be increased and material permeability of the shell may be lowered, thereby stably loading the oil. More specifically, the average particle diameter ($D_{50}$) of the microcapsule may be 5 μm or more, 6 μm or more, or 9 μm or more, and 30 μm or less, or 15 μm or less, and the average thickness of the shell containing the melamine-formaldehyde resin may be 60 nm or more, or 80 nm or more. The thicker the thickness, the more the effect may be enhanced. The thickness of the shell may also be 1000 nm or less, 800 nm or less, or 500 nm or less.

The average particle diameter ($D_{50}$) of the microcapsule can be calculated from a volume cumulative value measured with a laser diffraction scattering particle size analyzer, and the thickness of the capsule can be measured using an electron microscope.

According to another embodiment of the present disclosure, there is provided a microcapsule prepared by the above-described method.

As described above, the microcapsule has a core-shell structure including a core containing an oil surrounded by hydrophilic inorganic nanoparticles in which melamine is surface-bonded by electrostatic attraction; and a shell surrounding the core and containing a melamine-formaldehyde resin. Herein, the melamine, the hydrophilic inorganic nanoparticles, the oil and the melamine-formaldehyde resin are the same as described above.

In addition, the microcapsule may have an average particle diameter ($D_{50}$) of 5 μm to 50 μm. The average thickness of the shell may be 50 nm or more, or 60 to 1000 nm, and the shell may have a multi-layer structure.

Further, the microcapsule may contain 0.1 to 2 wt % of the hydrophilic inorganic nanoparticles, 1 to 4 wt % of the melamine, 5 to 60 wt % of the melamine-formaldehyde resin and 35 to 90 wt % of the oil based on a total weight of the microcapsule, and specifically contain 0.3 to 2 wt % of the hydrophilic inorganic nanoparticles, 1.5 to 3.5 wt % of the melamine, 10 to 60 wt % of the melamine-formaldehyde resin and 35 to 88 wt % of the oil based on a total weight of the microcapsule. More specifically the microcapsule may contain 0.5 to 1.8 wt % of the hydrophilic inorganic nanoparticles, 2 to 3.2 wt % of the melamine, 12 to 25 wt % of the melamine-formaldehyde resin and 70 to 85 wt % of the oil based on a total weight of the microcapsule.

Hereinafter, the function and effect of the present invention will be described in more detail through specific examples. However, these examples are for illustrative purposes only, and the invention is not intended to be limited by these examples.

Example 1: Preparation of Microcapsule

After dispersing silica nanoparticles as hydrophilic inorganic nanoparticles in water, diluted aqueous solution of hydrochloric acid (0.1 N) was added to adjust the pH to 5.0 to prepare an aqueous dispersion of the silica nanoparticles (average particle diameter of dispersed silica nanoparticles ($D_{50}$): 25 nm, content of silica nanoparticles in aqueous dispersion: 0.1 wt %). Separately, after melamine was dissolved in water, diluted aqueous solution of hydrochloric acid (0.1 N) was added to adjust the pH to 5.0 to prepare a melamine aqueous solution (content of melamine in melamine aqueous solution: 1.0 wt %). The aqueous dispersion of silica nanoparticles and the melamine aqueous solution prepared above were mixed so that a weight ratio of silica nanoparticles to melamine was 1:5 (0.02 g of silica nanoparticles and 0.10 g of melamine), thereby preparing a dispersion containing organic/inorganic nanocomposite in which melamine molecules are bonded at the surface of silica nanoparticles by electrostatic attraction. To 25 ml of the dispersion containing the organic/inorganic nanocomposite, 3.0 g of geraniol was added as a fragrance oil and mixed to prepare an oil-in-water pickering emulsion. 10.0 g of a solution (pH 6.0) in which 1.0 g of melamine-formaldehyde precondensate (MF) was diluted in water was slowly added to the resulting oil-in-water pickering emulsion (weight ratio of melamine:melamine-formaldehyde precondensate in oil-in-water pickering emulsion is 1:10, molar ratio of formaldehyde/melamine in melamine-formaldehyde precondensate is 6), and heated and stirred at 50° C. and 600 rpm to prepare a microcapsule. Herein, a content of the silica nanoparticles was 0.5 wt %, a content of the melamine was 2.4 wt %, a content of the melamine-formaldehyde resin was 24 wt %, and a content of the fragrance oil was 73.1 wt % based on a total weight of the microcapsule.

Example 2: Preparation of Microcapsule

After dispersing silica nanoparticles in water, diluted aqueous solution of hydrochloric acid (0.1 N) was added to adjust the pH to 5.0 to prepare an aqueous dispersion of the silica nanoparticles (average particle diameter of dispersed silica nanoparticles ($D_{50}$): 25 nm, content of silica nanoparticles in aqueous dispersion: 0.1 wt %). Separately, after melamine was dissolved in water, diluted aqueous solution of hydrochloric acid (0.1 N) was added to adjust the pH to 5.0 to prepare a melamine aqueous solution (content of melamine in melamine aqueous solution: 1.0 wt %). A dispersion containing silica nanocomposite was prepared in the same manner as in Example 1. To 25 ml of the dispersion containing the organic/inorganic silica nanocomposite, 3.0 g of geraniol was added as a fragrance oil and mixed to prepare an oil-in-water pickering emulsion. 10.0 g of a solution (pH 6.0) in which 0.5 g of melamine-formaldehyde precondensate (MF) was diluted in water was slowly added to the resulting oil-in-water pickering emulsion (weight ratio of melamine:melamine-formaldehyde precondensate in oil-in-water pickering emulsion is 1:5, molar ratio of formaldehyde/melamine in melamine-formaldehyde precondensate is 6), and heated and stirred at 50° C. and 600 rpm to prepare a microcapsule. A content of the silica nanoparticles was 0.55 wt %, a content of the melamine was 2.8 wt %, a content of the melamine-formaldehyde resin was 14 wt %, and a content of the fragrance oil was 82.65 wt % based on a total weight of the microcapsule.

Example 3: Preparation of Microcapsule

After dispersing titania nanoparticles in water, diluted aqueous solution of hydrochloric acid (0.1 N) was added to adjust the pH to 7.0 to prepare an aqueous dispersion of the titania nanoparticles (average particle diameter of dispersed $TiO_2$ nanoparticles ($D_{50}$): 20 nm, content of titania nanoparticles in aqueous dispersion: 1.0 wt %). Separately, after melamine was dissolved in water, diluted aqueous solution of hydrochloric acid (0.1 N) was added to adjust the pH to 5.0 to prepare a melamine aqueous solution (content of melamine in melamine aqueous solution: 1.0 wt %). A dispersion containing titania nanocomposite was prepared in the same manner as in Example 1. To 25 ml of the dispersion containing the organic/inorganic titania nanocomposite, 5.0 g of geraniol was added as a fragrance oil and mixed to prepare an oil-in-water pickering emulsion. 10.0 g of a solution (pH 6.0) in which 0.5 g of melamine-formaldehyde precondensate (MF) was diluted in water was slowly added to the resulting oil-in-water pickering emulsion (weight ratio of melamine:melamine-formaldehyde precondensate in oil-in-water pickering emulsion is 1:5, molar ratio of formaldehyde/melamine in melamine-formaldehyde precondensate is 6), and heated and stirred at 50° C. and 600 rpm to prepare a microcapsule. A content of the titania nanoparticles was 1.67 wt %, a content of the melamine was 2.5 wt %, a content of the melamine-formaldehyde resin was 12.5 wt %, and a content of the fragrance oil was 83.33 wt % based on a total weight of the microcapsule.

Example 4: Preparation of Microcapsule

After dispersing silica nanoparticles in water, diluted aqueous solution of hydrochloric acid (0.1 N) was added to adjust the pH to 5.0 to prepare an aqueous dispersion of the silica nanoparticles (average particle diameter of dispersed silica nanoparticles ($D_{50}$): 25 nm, content of silica nanoparticles in aqueous dispersion: 0.1 wt %). Separately, after melamine was dissolved in water, diluted aqueous solution of hydrochloric acid (0.1 N) was added to adjust the pH to 5.0 to prepare a melamine aqueous solution (content of melamine in melamine aqueous solution: 1.0 wt %). A dispersion containing silica nanocomposite was prepared in the same manner as in Example 1. To 25 ml of the dispersion containing the organic/inorganic silica nanocomposite, 3.0 g of n-hexadecane in which 1% nile red was dispersed was added and mixed to prepare an oil-in-water pickering emulsion. 10.0 g of a solution (pH 6.0) in which 0.5 g of melamine-formaldehyde precondensate (MF) was diluted in water was slowly added to the resulting oil-in-water pickering emulsion (weight ratio of melamine:melamine-formaldehyde precondensate in oil-in-water pickering emulsion is 1:5, molar ratio of formaldehyde/melamine in melamine-formaldehyde precondensate is 6), and heated and stirred at 50° C. and 600 rpm to prepare a microcapsule. A content of the silica nanoparticles was 0.55 wt %, a content of the melamine was 2.8 wt %, a content of the melamine-formaldehyde resin was 14 wt %, and a content of the oil for color formation was 82.65 wt % based on a total weight of the microcapsule.

Comparative Example 1: Preparation of Single Layer Microcapsule of Melamine-Formaldehyde Resin To 100 mL of an aqueous solution containing 1.6 g of SMA (styrene maleic anhydride), 20 g of geraniol was added as a fragrance oil and mixed to prepare an emulsion. 5.0 g of melamine-formaldehyde precondensate was added to the emulsion, and heated and stirred at 50 to 70° C. and 600 rpm to prepare a microcapsule.

Comparative Example 2: Preparation of Microcapsule Stabilized with Silica Nanoparticles To 100 ml of an aqueous dispersion containing silica nanoparticles (average particle diameter of silica nanoparticles ($D_{50}$): 25 nm, content of silica nanoparticles in aqueous dispersion: 0.1 wt %), 20 g of geraniol was added as a fragrance oil and mixed to prepare an oily pickering emulsion. 1.6 g of SMA (styrene maleic anhydride copolymer) was added as a surfactant to the emulsion and mixed to prepare a stable colloidal solution.

Comparative Example 3: Preparation of Silica-(Melamine-Formaldehyde Resin) Nanocomposite Emulsion After dispersing silica nanoparticles in water, diluted aqueous solution of hydrochloric acid (0.1 N) was added to adjust the pH to 5.0 to prepare an aqueous dispersion of the silica nanoparticles (average particle diameter of dispersed silica nanoparticles ($D_{50}$): 25 nm, content of silica nanoparticles in aqueous dispersion: 0.1 wt %). Separately, after dissolving melamine-formaldehyde precondensate (molar ratio of formaldehyde/melamine in melamine-formaldehyde precondensate is 6) in water, diluted aqueous solution of hydrochloric acid (0.1 N) was added to adjust the pH to 6.0 to prepare an aqueous solution (content of melamine-formaldehyde precondensate: 0.2 wt %). The aqueous dispersion of silica nanoparticles and the aqueous solution of melamine-formaldehyde precondensate prepared above were mixed so that a weight ratio of silica nanoparticles to melamine-formaldehyde precondensate was 1:2.5 (0.02 g of silica nanoparticles and 0.05 g of melamine-formaldehyde precondensate), thereby preparing a dispersion containing organic/inorganic silica nanocomposite in which melamine-formaldehyde precondensate is bonded at the surface of silica nanoparticles by electrostatic attraction. To 25 ml of the dispersion containing the organic/inorganic nanocomposite, 3.0 g of geraniol was added as a fragrance oil and mixed to prepare an oil-in-water pickering emulsion.

A microcapsule manufacturing process was carried out in the same manner as in Example 1 except for using the oil-in-water pickering emulsion prepared above, but no particles were formed.

Comparative Example 4

After dispersing silica nanoparticles in water, diluted aqueous solution of hydrochloric acid (0.1 N) was added to adjust the pH to 7.0 to prepare an aqueous dispersion of the silica nanoparticles (average particle diameter of dispersed silica nanoparticles ($D_{50}$): 25 nm, content of silica nanoparticles in aqueous dispersion: 0.1 wt %). Formaldehyde was added to the solution (silica:formaldehyde aqueous solution=1:25) to ensure surface reactivity of the silica particles. Separately, melamine was dissolved in water (content of melamine in aqueous melamine solution: 1.0 wt %). This was added to the mixture to induce a reaction of the surface of modified silica particles and melamine molecules, thereby forming a melamine layer in which melamine is chemically bonded to the surface of the silica particles. To 25 ml of the dispersion containing the organic/inorganic silica nanocomposite, 3.0 g of geraniol was added as a fragrance oil and mixed to prepare an oil-in-water pickering emulsion. 10.0 g of a solution (pH 6.0) in which 0.5 g of melamine-formaldehyde precondensate (MF) was diluted in water was slowly added to the resulting oil-in-water pickering emulsion (weight ratio of melamine:melamine-formaldehyde precondensate in oil-in-water pickering emulsion is 1:5, molar ratio of formaldehyde/melamine in melamine-formaldehyde precondensate is 6), and heated and stirred at 50° C. and 600 rpm in order to prepare a microcapsule. However, no particles were formed, and amorphous aggregation was formed.

Reference Example 1: Preparation of Microcapsule Consisting of Silica Nanoparticles and Acrylate Composite A silica colloidal solution was prepared by dispersing 0.4 g of silica nanoparticles (average particle diameter ($D_{50}$): 25 nm) in 50 mL of water, and then 3 g of diethylene glycol diacrylate having a solubility in water of about 25 g/L was added thereto, followed by ultrasonic dispersion for 20 minutes in an ice bath. Accordingly, the acrylate monomer was bonded to the surface of silica by electrostatic attraction.

20 g of geraniol was added to 100 mL of the resulting solution as a fragrance oil in which an oil-soluble initiator was dissolved, followed by ultrasonic dispersion for 20 minutes in an ice bath to prepare a pickering emulsion. This was placed in a round flask and sealed, and then subjected to $N_2$ bubbling and a radical polymerization reaction at 60° C. for 20 hours to prepare a microcapsule.

Experimental Example 1

The microcapsule prepared in Example 1 was observed with an optical microscope, and the result is shown in FIG. 1.

It was confirmed that the microcapsule prepared in Example had a core-shell structure in which an oil surrounded by silica nanoparticles in which melamine is surface-bonded by electrostatic attraction forms the core, and a melamine-formaldehyde resin forms the shell surrounding the core.

Experimental Example 2

The pickering emulsions prepared in Examples 1, 3 and Comparative Example 3 were observed with an optical microscope, and the results are shown in FIGS. 2 to 4.

The oil-in-water pickering emulsions prepared in Examples 1 and 3 had a uniform size of organic/inorganic composite particles in which melamine molecules are bonded at the surface of silica nanoparticles by electrostatic attraction, whereas the oil-in-water pickering emulsion prepared in Comparative Example 3, using melamine-formaldehyde precondensate in place of the melamine monomolecular compound in Example 1, had a small and non-uniform size of organic/inorganic composite particles.

Experimental Example 3

Particle characteristics of the microcapsules prepared in Examples, Comparative Examples and Reference Example were evaluated according to the following methods.

(1) Shape: The shape of capsules was observed with an electron microscope, and the results are shown in FIGS. 5 to 12, respectively.
(2) Average particle diameter ($D_{50}$): It was measured with a laser diffraction scattering particle size analyzer twice or more times, and calculated from a volume cumulative value. The results are expressed as mean±standard deviation.
(3) Compressed shape: It was pressed vertically with 1 N/cm² to observe the degree of crushing and the shape of capsule (S-4800, manufactured by Hitachi), and classified as follows.
A: broken
B: torn
C: pressed
(4) Shell thickness: It was measured with an electron microscope (HITACHI S-4800).

In addition, washing durability was evaluated by the following method of evaluating the residual scent.
(5) Evaluation of adhesion to fibers of particles:

Assuming that loading capacity and efficiency of each fragrance capsule are the same, the adhesion to fibers of the fragrance capsule was evaluated by evaluating the residual scent in the washed fibers.

<Test Conditions (Evaluation with General Washing Machine)>

The test specimen was prepared by using commercially available 100% cotton towel (30×20 cm) and blended fabric for evaluating the residual scent (30×20 cm), and then washed five times with a washing machine using general laundry detergent in a standard amount, followed by dehydration.

Each microcapsule prepared in the above Examples, Comparative Examples and Reference Example was made into a 1% aqueous solution, and then used in rinsing water (20° C.) in a standard amount (0.67 ml/1 L washing water) to run a rinse course in a stirring washing machine. Thereafter, the test specimen was taken out after dehydration. Then, the specimen was flat-dried for 24 hours at 20° C. and 60% RH without stretching or warping. An experienced panelist's sensory evaluation test gave the intensity of the fragrance a score from 1 to 5, and the test was repeated three times or more to obtain an average value, which was used to evaluate the residual scent effect. Other detailed test conditions are in accordance with the test method in EL306 (Fiber Softener) of the Eco-Labeling Certification Standard of Korea Environmental Industry and Technology Institute.

(6) Residual scent after drying:

If an amount of fragrance oil loaded per capsule is large, the residual scent may be excellent even if the adhesion to fibers is not superior. In order to compare the amount of fragrance oil loaded in the microcapsule, the residual scent was evaluated after drying.

Each microcapsule prepared in the above Examples, Comparative Examples and Reference Example was made into a 1% aqueous solution, and the test specimen prepared above was added thereto, impregnated for 1 hour, taken out and then dried. The residual scent of the fragrance capsule was evaluated by evaluating the residual scent of the test specimen after drying. As described above, an experienced panelist's sensory evaluation test gave the intensity of the fragrance a score from 1 to 5, and the test was repeated three times or more to obtain an average value, which was used to evaluate the residual scent effect. However, Comparative Examples 3 and 4 were excluded from the evaluation, because no particles were formed.

TABLE 1

|  | Ex. 1 | Ex. 2 | Ex. 3 | Comp. Ex. 1 | Comp. Ex. 2 | Ref. Ex. 1 |
| --- | --- | --- | --- | --- | --- | --- |
| Average particle diameter ($D_{50}$, μm) (mean ± standard deviation) | 10 ± 5 | 9 ± 3 | 21 ± 3 | 3 ± 2 | 3 ± 2 | 6 ± 3 |
| Compressed shape | A | A | B | C | C | C |
| Shell thickness (nm) | 100 | 80 | 200 | <50 | <50 | <50 |
| Adhesion to fibers of particles | 4 | 4 | 3 | 3 | 2 | 2 |
| Residual scent after drying | 4 | 3 | 3 | 3 | 1 | 2 |

Referring to the results, the microcapsules of Examples 1 to 3 prepared according to the present disclosure had an average particle diameter of 5 μm or more and an average thickness of the shell of 80 to 200 nm. That is, they had larger capsules and thicker films, and exhibited higher hardness, compared to the microcapsules of Comparative Examples 1 and 2 prepared by the conventional method, and the capsule of Reference Example 1 consisting of silica nanoparticles and acrylate composite. From this, it can be seen that the microcapsules of Examples 1 to 3 may contain a fragrance oil at a higher content, further reduce material permeability through the capsule film, and stably load the fragrance oil due to high durability, compared to Comparative Examples 1 and 2, and Reference Example 1. This improvement effect was confirmed from the evaluation of the adhesion to fibers and the residual scent after drying.

In addition, the oil-in-water pickering emulsion prepared in Example 4, the final microcapsule and the aqueous dispersion in which the capsule was dispersed were observed, respectively, and the results are shown in FIGS. 13 to 15.

FIG. 13 is an optical microscope observation image of the oil-in-water pickering emulsion prepared in Example 4.

As shown in FIG. 13, even in the case of including an oil for color formation instead of the fragrance oil, an oil-in-water pickering emulsion was formed as in Examples 1 and 3, and the size of organic/inorganic composite particles in which melamine molecules are bonded to the surface of silica nanoparticles by electrostatic attraction was uniform.

FIG. 14 is a photograph of the aqueous dispersion of the microcapsule prepared in Example 4, and FIG. 15 is a fluorescence microscope image of the microcapsule prepared in Example 4.

Referring to the results, the microcapsule prepared in Example 4 also had a core-shell structure in which an oil surrounded by silica nanoparticles in which melamine is surface-bonded by electrostatic attraction forms the core, and a melamine-formaldehyde resin forms the shell surrounding the core. In addition, it exhibited a red color due to nile red contained in the oil of the core. It was confirmed that the reaction of the oil for color formation could be inhibited even in the state of aqueous dispersion due to the microcapsule structure, thereby maintaining the performance for a long time.

The invention claimed is:
1. A method for preparing a microcapsule, comprising
a first step of mixing an aqueous dispersion of hydrophilic inorganic nanoparticles with an aqueous solution of a melamine-based monomolecular compound to prepare an aqueous dispersion of organic/inorganic composite particles in which melamine is bonded to a surface of the hydrophilic inorganic nanoparticles by electrostatic attraction;

a second step of adding an oil to the aqueous dispersion of organic/inorganic composite particles to form an oil-in-water pickering emulsion; and a third step of adding a melamine-formaldehyde precondensate to the oil-in-water pickering emulsion, and performing a polycondensation reaction, wherein the hydrophilic inorganic nanoparticles comprise silica, or titania, the aqueous dispersion of hydrophilic inorganic nanoparticles has a pH of 4 to 7, the aqueous solution of a melamine-based monomolecular compound has a pH of 4 to 7, the mixing of the aqueous dispersion of hydrophilic inorganic nanoparticles with the aqueous solution of the melamine-based monomolecular compound is performed so that a content of the melamine-based monomolecular compound is 2 to 5 parts by weight based on 1 part by weight of the hydrophilic inorganic nanoparticles, the melamine-formaldehyde precondensate is added in an amount such that a content of a melamine-formaldehyde resin is 5 to 60 wt % based on a total weight of the microcapsule to be prepared; and the microcapsule has a core-shell structure comprising: a core comprising an oil surrounded by hydrophilic inorganic nanoparticles in which melamine is surface-bonded by electrostatic attraction; and a shell surrounding the core and comprising a melamine-formaldehyde resin, and wherein the microcapsule comprises 1 to 4 wt % of the melamine based on a total weight of the microcapsule.

2. The method for preparing a microcapsule of claim 1, wherein the hydrophilic inorganic nanoparticles have an average particle diameter ($D_{50}$) of 1 to 300 nm.

3. The method for preparing a microcapsule of claim 1, wherein the oil is a fragrance oil, an oil for color formation, or a mixture thereof.

4. The method for preparing a microcapsule of claim 3, wherein the fragrance oil is an essential oil, a mineral oil, or a vegetable oil.

5. The method for preparing a microcapsule of claim 3, wherein the oil for color formation comprises an oil dispersion coloring agent and a nonpolar hydrocarbon-based oil.

6. The method for preparing a microcapsule of claim 5, wherein the oil dispersion coloring agent comprises nile red, fluorescein, rhodamine, boron-dipyrromethene, a cyanine-based organic compound, quantum dot, or a mixture thereof.

7. The method for preparing a microcapsule of claim 1, wherein the oil is added in an amount of 35 to 90 wt % based on a total weight of the microcapsule to be prepared.

8. The method for preparing a microcapsule of claim 1, wherein the melamine-formaldehyde precondensate is added in an amount such that a content of a melamine-formaldehyde resin is 10 to 60 wt % based on a total weight of the microcapsule to be prepared.

9. The method for preparing a microcapsule of claim 1, wherein a molar ratio of formaldehyde to melamine in the melamine-formaldehyde precondensate is 2 to 8.

10. The method for preparing a microcapsule of claim 1, wherein the polycondensation reaction is carried out at a temperature of 50 to 90° C.

* * * * *